United States Patent [19]

Moss et al.

[11] Patent Number: 5,770,210
[45] Date of Patent: Jun. 23, 1998

[54] RECOMBINANT VACCINIA VIRUS EXPRESSING HUMAN RETROVIRUS GENE

[75] Inventors: Bernard Moss, Bethesda, Md.; Sekhar Chakrabarti, Nabagram, India

[73] Assignee: The United States of America as represented by the Department of Health and Human Services, Washington, D.C.

[21] Appl. No.: 919,384

[22] Filed: Jul. 29, 1992

Related U.S. Application Data

[63] Continuation of Ser. No. 377,750, Jul. 7, 1989, abandoned, which is a continuation of Ser. No. 849,298, Apr. 8, 1986, abandoned.

[51] Int. Cl.$^6$ ...................... A61K 39/21; A61K 39/295; C12N 15/86; C12P 21/02

[52] U.S. Cl. ................... 424/199.1; 424/93.2; 435/69.3; 435/320.1

[58] Field of Search ............................... 435/69.3, 320.1; 424/199.1, 93.2

[56] References Cited

U.S. PATENT DOCUMENTS

| | | | |
|---|---|---|---|
| 4,603,112 | 7/1986 | Paoletti et al. | 435/235.1 |
| 5,081,029 | 1/1992 | Zarling et al. | 435/172.3 |

OTHER PUBLICATIONS

Cremer et al., (1985) Science 228:737–740.
Mackett et al., (1985) Science 227:433–435.
Wicktor et al., (1984) Proc. Natl. Acad. Sci. USA 81:7194–98.
Moss et al., (1984) Nature 311:67–69.
Wain–Hobson et al., (1985) Cell 40:9–17.
Sanchez–Pescador et al., (1985) Science 227:484–492.
Ratner et al., (1985) Nature 313:277–284.
Muesing et al., (1985) Nature 313:450–458.
Robey et al., (1985) Science 228:593–595.
Veronese et al., (1985) Science 229:1402–1405.
Crowl et al., (1985) Cell 41:979–986.
Panicali et al., (1983) Proc. Natl. Acad. Sci. USA 80:5364–68.
Smith et al., (1983) Proc. Natl. Acad. Sci. USA 80:7155–7159.
Lizhong et al., "Expression of the M Gene of Vesicular Stomatitis Virus Cloned in Various Vaccinia Virus Vectors", Journal of Virology vol. 62: Mar. 1988, pp. 776–782.
Lifson et al., "Induction of CD4–dependent cell fusion by the HTLV–III/LAV envelope glycoprotein", Nature, vol. 323, Oct. 23, 1986, pp. 725–728.
Sodroski et al., "A second post-transcriptional trans-activator gene required for HTLV–III replication", Nature, vol. 321, May 22, 1986, pp. 412–417.
Peterlin et al., "Elevated levels of mRNA can account for the trans–activation of human immunodeficiency virus", Proc. Natl. Acad. Sci. USA, vol. 83, Dec. 1986, pp. 9734–9738.
Rosen et al., "Post–transciprtional regulation accounts for the trans–activation of the human T–lymphotropic virus type III", Nature, vol. 319, Feb. 13, 1986, pp. 555–559.
Langford et al., "Anchoring a Secreted Plasmodium Antigen on the Surface of Recombinant Vaccinia Virus–Infected Cells Increases Its Immunogenicity", Molecular and Cellular Biology vol. 6: Sep. 1986, pp. 3191–3199.
Berman et al., "Expression of Membrance–Associated and Secreted Variants of gp160 of Human Immunodeficiency Virus Type 1 in Vitro and in Continuous Cell Lines", Journal of Virology vol. 62: Sep. 1988, pp. 3135–3142.
Falkner et al., "Use of Vaccinia Virus Vectors to Study the Synthesis, Intracellular Localization, and Action of the Human Immunodeficiency Virus Trans–Activator Protein", Virology 164, pp. 450–457 (1988).
Elango, N. et al (1986) Proc. Natl. Acad. Sci. USA 83:1906–1910.
Stephens, E.B. et al (1986) The EMBO Journal 5:237–245.
Mackett, M. et al. (1985) The EMBO Journal 4:3229–3234.

*Primary Examiner*—George C. Elliott
*Assistant Examiner*—Johnny F. Railey, II
*Attorney, Agent, or Firm*—Merchant, Gould, Smith, Edell, Welter & Schmidt, P.A.

[57] ABSTRACT

A recombinant vaccinia virus capable of expressing HTLV-III envelope protein (env) has been constructed. The expressed env protein is recognized by sera obtained from AIDS patients. The synthesized env protein also produces antibodies when administered to a suitable host, such antibodies having specific binding affinity with the env protein.

5 Claims, 5 Drawing Sheets

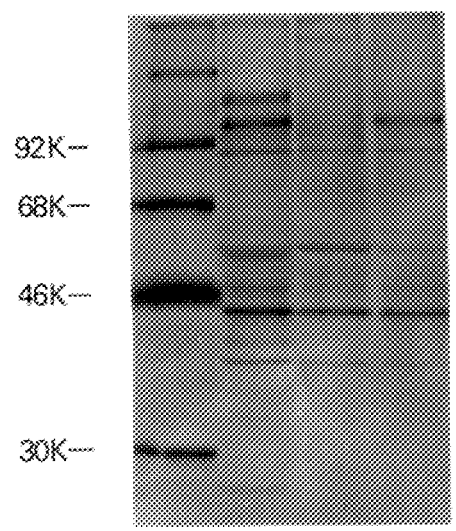
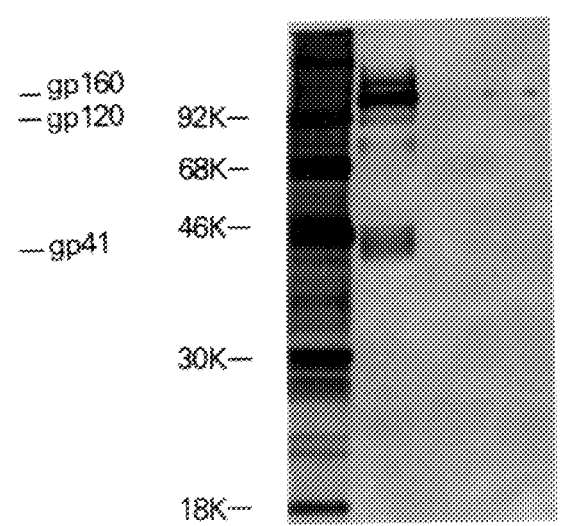

RECOMBINANT VACCINIA VIRUS EXPRESSING HUMAN RETROVIRUS GENE

This application is a continuation of application Ser. No. 07/377,750, filed Jul. 7, 1989, now abandoned, which is a continuation of application Ser. No. 06/849,298, filed Apr. 8, 1986 now abandoned.

BACKGROUND OF THE INVENTION

1. Technical Field

The present invention is related to the synthesis of envelope protein of human T-lymphotropic virus type III (HTLV-III). More particularly, the present invention is related to recombinant vaccinia virus capable of expressing HTLV-III envelope gene and inducing antibodies to the envelope proteins in a susceptible host.

2. State of The Art

The etiological agent of acquired immune deficiency syndrome (AIDS) is recognized to be a retrovirus, referred to as HTLV-III. It has been reported that the envelope proteins of murine retroviruses can induce protective immunity in mice (Hunsmann et al., Virology Holman & Stern, Chartered Folio P49625 113:602–612, 1981;). The HTLV-III gene for envelope proteins (env) is believed to specify a primary polypeptide of about 860 amino acids that is glycosylated to form in terms of relative molecular weight (Mr) a 160,000 (gp 160) precursor to mature Mr 120,000 (gp120) and 41,000 (gp41) membrane-associated proteins (Wain-Hobson et al., Cell 40:9–17, 1985; Sanchez-Pescador et al., Science 227:484–492,1985; Ratner et al., Nature 313:277–284, 1985; Muesing et al., Nature 313:450–458, 1985; Robey et al., Science 228:593–595, 1985; Veronese et al., Science 229:1402–1405, 1985). A large portion of the HTLV-III env gene has been expressed in *Escherichia coli* (Crowl et al., Cell 41:979–986, 1985). Although antigenic, the polypeptide synthesized by *E. coli* was smaller than the primary virus protein and was neither glycosylated nor processed by bacteria. The HTLV-III env gene has also been cloned into a eukaryotic SV40 transient expression vector but the product was characterized only by indirect immunofluorescence of fixed cells (Sanchez-Pescador, supra).

Vaccinia virus is a particularly useful eucaryotic vector system for producing live recombinants capable of expressing foreign genes. Surface antigen genes from a variety of DNA and RNA viruses have been expressed by recombinant vaccinia viruses. (Panicali et al., Proc. Natl. Acad. Sci. USA 80:5364–5368, 1983; Smith et al., Proc. Natl. Acad. Sci. USA 80:7155–7159, 1983; Paoletti et al., Proc. Natl. Acad. Sci. USA 80:5364–5368, 1984; Moss et al., Nature 311:67–69, 1984; Wiktor et al., Proc. Natl. Acad. Sci. USA 81:7194–7198, 1984; Mackett et al., Science 227:433–435, 1985; Cremer et al., Science 228:737–739, 1985). When properly engineered, the proteins are synthesized, processed and transported to the plasma membrane. In some cases, experimental animals produce neutralizing antibodies and are protected against a challenge with the corresponding virus. Evidence for priming of a cytotoxic T cell response has also been obtained with recombinant vaccinia viruses that express influenza virus genes. Despite such developments cloning and expression of complete HTLV-III env gene by a vaccinia virus or other vector has not heretofore been achieved.

SUMMARY OF THE INVENTION

It is, therefore, an object of the present invention to provide recombinant plasmid carrying the gene encoding complete HTLV-III envelope precursor protein.

It is a further object of the present invention to provide recombinant vaccinia virus capable of expressing HTLV-III envelope proteins.

It is a still further object of the present invention to provide a system for synthesis, processing and membrane transport of the env polypeptides without other HTLV-III gene functions.

It is yet another object of the present invention to synthesize HTLV-III env proteins which are recognized by sera from unrelated AIDS patients.

It is a still further object of the present invention to induce antibodies against HTLV envelope proteins in a susceptible host by administering to said host an effective amount of recombinant vaccinia virus carrying env gene so as to produce said antibodies.

It is another object of the present invention to provide a method of producing HTLV-III envelope proteins comprising the steps of propagating the recombinant vaccinia virus of the present invention in a growth medium comprising cultured cells which support multiplication of the recombinant virus and recovering the env proteins expressed by the recombinant virus from the cells and growth medium.

Other objects and advantages will become evident as the detailed description of the invention proceeds.

BRIEF DESCRIPTION OF DRAWINGS

These and other objects, features and many of the attendant advantages of the invention will be better understood upon a reading of the following detailed description when considered in connection with the accompanying drawings wherein:

FIG. 5A–B shows induction of antibodies to envelope proteins by immunization of mice with recombinant vaccinia virus. H9 cells were infected with HTLV-III and labeled with [$^{35}$S]methionine (panel A) or [$^3$H]glucosamine (panel B). The cell lysates were incubated with serum from an AIDS patient (lane 1), serum from a mouse that had been inoculated intraperitoneally with $10^8$ pfu of a recombinant vaccinia virus that contains the influenza hemagglutinin gene (lane 2) or HTLV-III env gene (lane 3). The proteins having specific affinity to antibodies and bound thereto were immunopurified with protein A Sepharose and analyzed by polyacrylamide gel electrophoresis as in FIG. 2B.

DETAILED DESCRIPTION OF INVENTION

The above and other objects and advantages of the present invention are achieved by a new vaccinia recombinant vector capable of expressing HTLV-III env proteins and a method of producing said env proteins by said recombinant vector.

Unless specifically defined otherwise, all scientific or technical terms used herein have the same meaning as generally understood by one of ordinary skill in the art to which the invention belongs. All publications cited hereunder are incorporated herein by reference.

It is noted that the methods and materials described herein are the preferred embodiments only and that any similar or equivalent methods and materials generally known in the art could be easily adapted and/or used in the practice of the invention or for the tests described herein.

The term "recombinant" as used herein means a genetic entity carrying a foreign gene combined, in whole or in part, in acceptor genome. Such a recombinant entity in the present application, for example, is a plasmid into the genome (DNA) of which a part or the whole of env factor (gene), has been inserted. In this example, the plasmid DNA provides the acceptor genome and the inserted env factor is the foreign gene.

In order to produce the recombinant virus, the essential steps are as follows. First, the segments of the vaccinia virus are inserted into suitable vectors of which plasmids are preferred. A DNA copy of the HTLV-III env gene is inserted in the plasmid under the control of a vaccinia viral promoter sequence and flanked by vaccinia viral sequences. Cells are infected with vaccinia virus, and the infected cells are transformed with the recombinant plasmids. Homologous recombinations of plasmid DNA and vaccinia virus DNA result in vaccinia viruses which incorporate the env sequences. Because insertion of the env sequence into the vaccinia virus sequence frequently destroys or truncates a vaccinia virus protein, thereby altering vaccinia viral function, recombinant vaccinia viruses are selectable from the wild type on the basis of this altered function (Chakrabarti et al., Mol. Cell. Biol. 5:3403–3409, 1985).

Methods and Material
Viruses and Cells.

Vaccinia virus (WR strain) was grown in HeLa cells and purified from cytoplasmic extracts by sucrose gradient centrifugation following standard procedures as described by Joklik, Virology 18:9–18 (1962).

Isolation of DNA.

DNA was isolated from purified vaccinia virus as described by Garon et al., Proc. Natl. Acad. Sci. USA 75:4863–4867 (1978). E. coli plasmid DNA was prepared using a modified alkaline-sodium dodecyl sulfate (SDS) procedure (Birnboim et al., Nucleic Acids Res. 7:1513–1523, 1979), wherein lysozyme was omitted from the lysis step and the DNA was purified from RNA by passage through a Sepharose-4B column. DNA fragments were purified from agarose gels by electroblotting onto DEAE paper (Winberg et al., Nucleic Acids Res. 8:253–264, 1980).

Construction of env-vaccinia recombinant.

Figure 1:
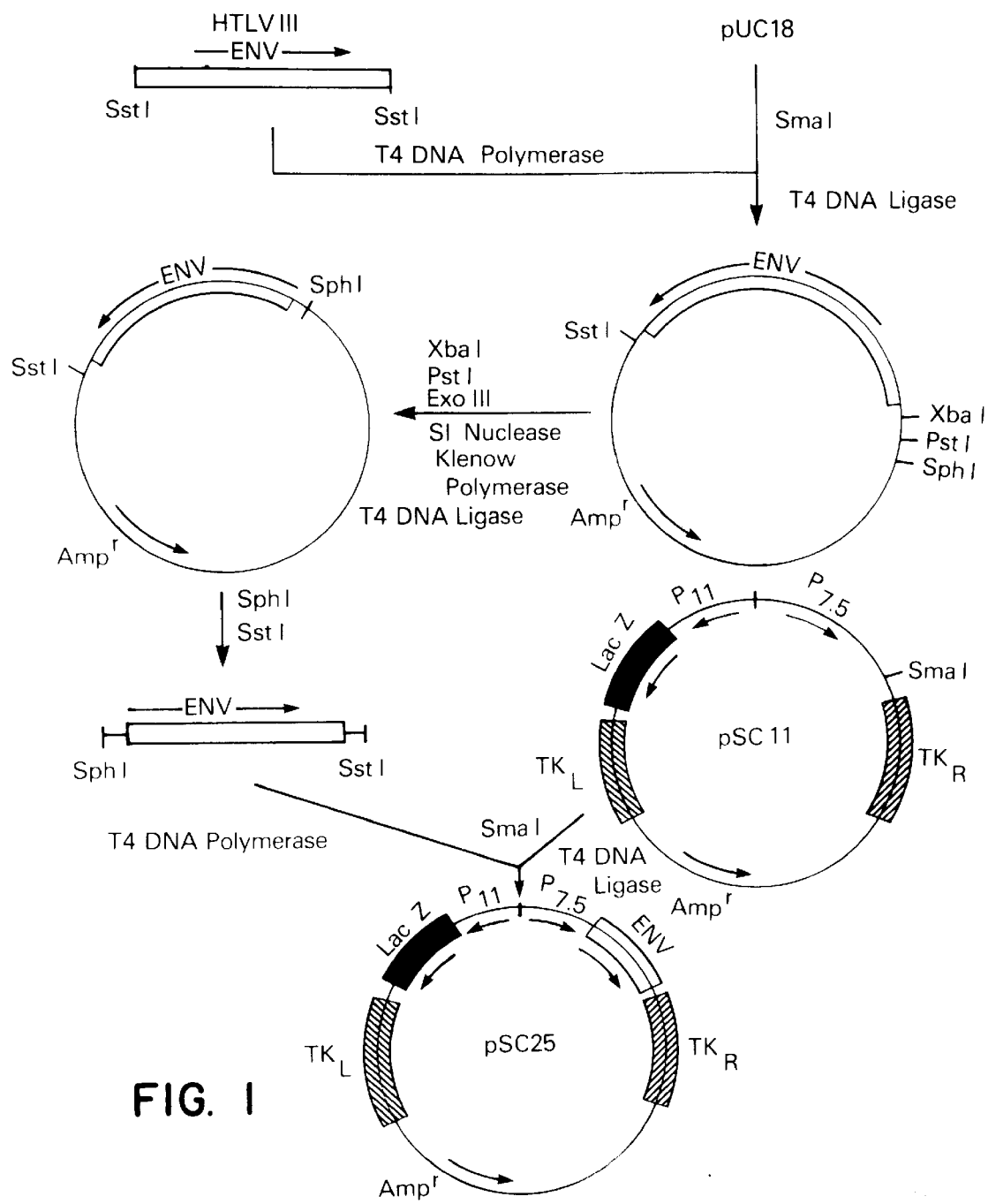
FIG. 1 outlines the steps used to construct a plasmid pSC25 used to insert the HTLV-III envelope gene into vaccinia virus.

A 3.5 kilobase pair SstI fragment of HTLV-III DNA was excised from λ clone BH8 (Ratner et al., Nature 313:277–284, 1985) blunt-ended with T4 DNA polymerase and cloned into the SmaI site of pUC18 so that the XbaI and pstI polylinker sites were located upstream of the env gene (FIG. 1). After cleavage with XbaI and PstI, unidirectional digestion with exonuclease III and S1 was carried out (Henikoff Gene 28;351–359, 1984). Blunt ends were created with the Klenow fragment of DNA polymerase and deoxyribonucleoside triphosphates and the plasmid were recircularized with T4 DNA ligase and used to transform E. coli. Plasmids from individual colonies were sequenced to determine the number of nucleotides remaining upstream of the env gene. DNA fragments containing the entire env gene were obtained by cleavage with SphI and SstI and inserted into the SmaI site of pSCll (Chakrabarti et al., Mol. Cell Biol. 5:3403–3409, 1985) to form pSC25 and pSC26 which have 0 or 70 bp of env leader sequence, respectively. Recombinant vaccinia viruses v25 and v26 that are both thymidine kinase negative and β-galactosidase positive were formed by homologous recombination using pSC25 and pSC26, respectively.

As noted above, DNA segments containing the entire HTLV-III env gene starting at or 70 bp upstream of the putative translation initiation codon were isolated and inserted into the SmaI site of pSC11 to obtain the env-vaccinia recombinant in accordance with the procedure described by Chakrabarti et al., Mol. Cell. Biol. 5:3403–3409 (1985). The plasmid vector has the following important features: a vaccinia virus promoter with early and late transcriptional signals just upstream of the SmaI site; the E. coli lacZ gene under control of a late vaccinia virus promoter; and flanking DNA containing the left and right halves of the vaccinia virus thymidine kinase (TK) gene. By transfecting cells that were infected with vaccinia virus, the HTLV-III env gene and the E. coli lacZ gene under control of separate vaccinia virus promoters were simultaneously introduced by homologous recombination into the TK locus of the vaccinia virus genome. Recombinant virus plaques were selected by their TK- phenotype and identified by formation of an intense blue color, due to expression of β-galactosidase, upon addition of an indicator to the agarose overlay.

A deposit of the recombinant vaccinia virus v25 (vSC25) carrying env gene has been made at the American Tissue Culture Collection, Rockville, Md. under the accession number VR2130. The deposit will continue to be maintained for at least 30 years when a patent issues and will be made available to the public without restriction, of course, consistent with the provisions of the law.

Figure 2A:
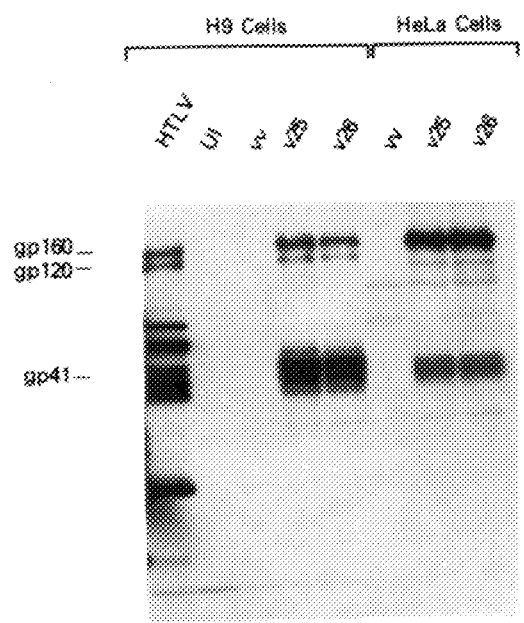
FIG. 2A–B demonstrates expression of HTLV-III env gene products by vaccinia virus recombinants. A. Immunoblot of HTLV env proteins from cells infected with vaccinia virus recombinants. H9 or HeLa cells were infected with 30 plaque forming units (pfu) of standard vaccinia virus (vv) or vaccinia recombinant viruses v25 or v26. Cells were harvested at 24 h after infection, lysed, and subjected to SDS-polyacrylamide (10%) gel electrophoresis. The polypeptides were transferred to a nitrocellulose membrane and incubated successively with serum from a patient with AIDS and $^{125}$I-protein A. The positions of authentic env proteins gp160, gp120 and gp41 were determined by electrophoresis of HTLV-III-infected H9 cell lysates in a parallel lane. Control uninfected (UI) cells were treated in a similar manner. B. Immunopurification of [$^3$H]glucosamine-labeled HTLV-III env proteins. H9 cells were infected with vv, v25 or v26 and metabolically labeled with [$^3$H]glucosamine from 2 to 24 h. Cell extracts were first incubated with normal donor serum and then protein-A Sepharose to remove proteins with non-specific binding affinity. After centrifugation, the supernatants were incubated with serum from a patient with AIDS and again with protein A-Sepharose. Proteins were eluted from the sepharose and resolved on a SDS-polyacrylamide (10%) gel and autoradiographed. The left lane shows marker proteins.

Protein Synthesis:

Synthesis of HTLV-III env proteins was demonstrated by polyacrylamide gel electrophoresis of lysates of cells infected with recombinant vaccinia viruses v25 and v26. These viruses differ only in the length of the non-translated leader sequence of the HTLV-III env gene. The expressed (synthesized) polypeptides can be separated or recovered from the culture medium by any standard procedure well known in the art such as chromatography, electrophoresis and the like. A sample of the separated polypeptides was transferred to nitrocellulose and incubated successively with serum from an AIDS patient and $^{125}$I-protein A. When H9 cells were used for infection, the 3 major bands detected by autoradiography co-migrated with authentic gp160, gp120 and gp41 (FIG. 2A). These polypeptides were not detected in lysates of either uninfected cells or cells infected with standard vaccinia virus. Bands corresponding to gp160 and gp41 but not gp120 were detected when HeLa cells (FIG. 2A) or CV-1 cells (not shown) were infected with recombinant vaccinia virus v25. A minor band migrating with an apparent Mr of about 100,000 and possibly representing a degraded or incompletely glycosylated form of gp120 was noted (FIG. 2A). Formation of gp120 was not specific for lymphocytes such as H9 cells that are permissive for replication of HTLV-III, since further studies showed that gp120 was also formed in NIH 3T3 cells that were infected with recombinant vaccinia virus. Replication of vaccinia virus does not appear to be a determining factor either, since all four cell lines were permissive for v25.

Figure 2B:
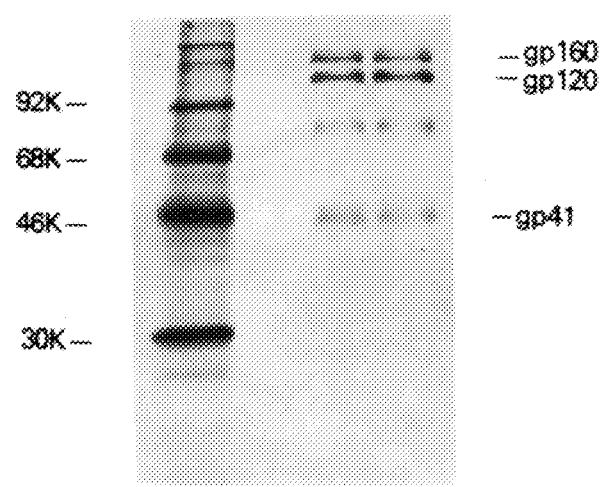

Based on the deduced amino acid sequence, there are approximately 20 potential N-glycosylation sites in the env protein. To demonstrate glycosylation of the HTLV-III polypeptides synthesized by recombinant vaccinia viruses, infected H9cells were metabolically labeled with [$^3$H]glucosamine and the proteins were incubated with serum from an AIDS patient and then bound to protein A Sepharose. An autoradiograph of a polyacrylamide gel (FIG. 2B) shows that glycosylated polypeptides corresponding to gp160, gp120 and gp41 were immunopurified. An additional glycosylated polypeptide with an Mr of approximately 80,000 also was detected. The nature of this polypeptide has not been established.

Figure 3:
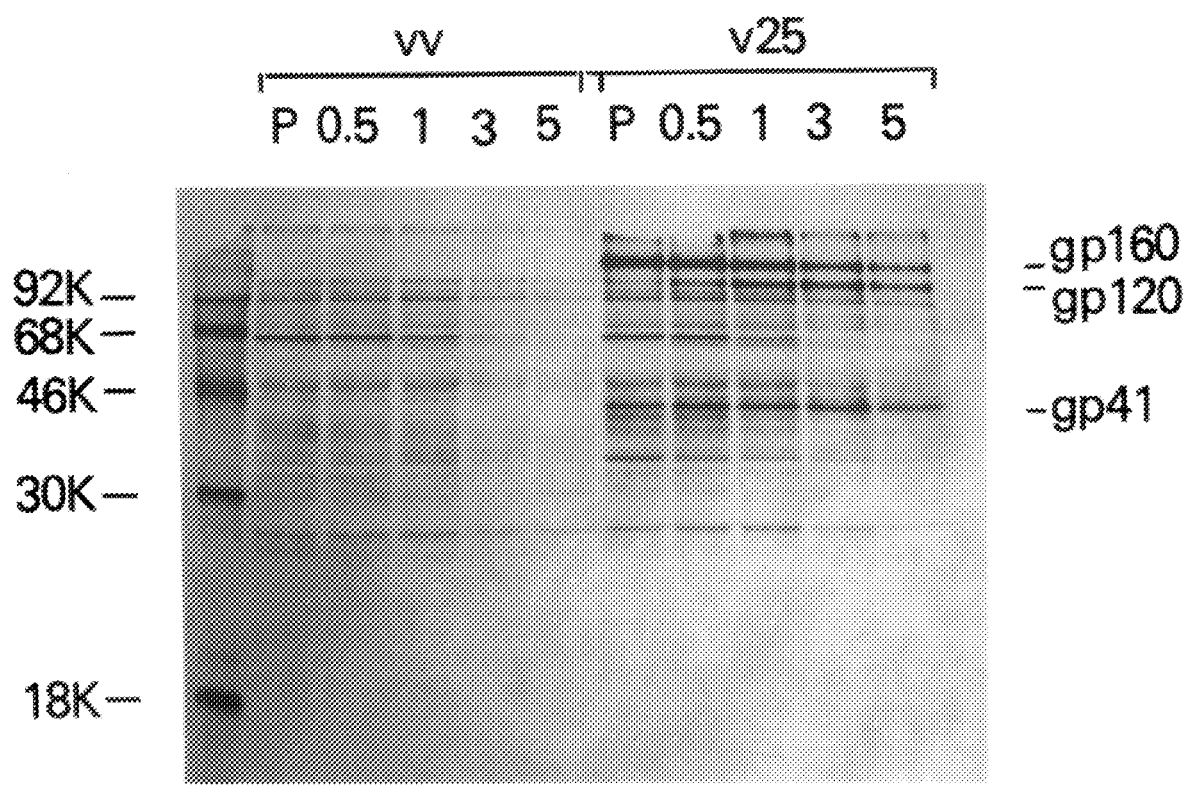
FIG. 3 shows synthesis and processing of HTLV-III env proteins. At 2 h after infection with wild-type (vv) or recombinant v25 vaccinia virus, the H9 cells were incubated for 1 h in methionine-free medium and then pulse-labeled with [$^{35}$S] methionine for 30 min. The cells were then resuspended in medium containing excess methionine for 0.5, 1, 2, 3, and 5 h time periods. Immunopurification and polyacrylamide gel electrophoresis was carried out as in FIG. 2B. The left lane shows marker proteins.

To determine the synthesis and processing of the env proteins, H9cells were infected with recombinant or standard vaccinia virus, pulse-labeled with [$^{35}$S]methionine for 30 min and then chased with excess unlabeled methionine. Labeled proteins from cell lysates were incubated with serum from a patient with AIDS, bound to protein A Sepharose and analyzed by polyacrylamide gel electrophoresis. Autoradiographs revealed a number of background bands common to both standard and recombinant vaccinia virus infected cells (FIG. 3). The band that was labeled most during the pulse-period, however, was specific to the recombinant virus infected cells and corresponded in size to gp160. The rapid labeling of the gp160 band and the apparent absence of an unglycosylated Mr 90,000 primary product indicate that synthesis and glycosylation are closely coupled events. During the chase pereiod, the gp160 band diminished in intensity while bands corresponding to gp120 and gp41 increased consistent with a precursor-product relationship.

Figure 4:
FIG. 4 shows detection of HTLV-III env protein on the surface of H9 cells infected with recombinant vaccinia virus. H9 cells, infected with 30 pfu/cell of v25 for 12 h, were collected by centrifugation, washed 3 times with phosphate buffered saline, and incubated for 30 min with patient serum that had been pre-adsorbed on vaccinia virus-infected H9 cells. After washing repeatedly with phosphate buffered saline, the cells were incubated with FITC-conjugated goat anti-human IgG and examined by fluorescence microscopy.

Since HTLV-III buds from the surface of infected cells, the env proteins are inserted into the plasma membrane. Indirect immunofluorescence was used to demonstrate that surface transport of HTLV-III env polypeptides also occurs in cells infected with recombinant vaccinia virus (FIG. 4). The AIDS serum used for this analysis had been preadsorbed with vaccinia virus-infected H9 cells and no discernible immunofluorescence was detected with either uninfected or vaccinia virus infected H9 cells (data not shown).

Because there are sequence variations in the env genes of independent virus isolates (Ratner et al., Nature 313:636–637, 1985; Benn et al., Science 230:949–951, 1985), it was important to determine whether the env protein expressed by recombinant vaccinia virus would react with sera from a variety of patients with AIDS. Using an assay similar to that in FIG. 2B, it was found that [$^3$H] glucosamine-labeled gp160 and gp120 had specific binding affinity with sera from 6 unrelated AIDS patients but not with sera from 2 normal volunteers. A strong band corresponding to gp41 also was obtained with the AIDS patients' sera. However, a faint band in the same position was also observed with normal sera.

Since epitopes that elicit neutralizing antibody are likely to reside in gp120, mice were inoculated with purified infectious recombinant virus containing the HTLV-III env gene or the influenza hemagglutinin. The experimental and control sera were then incubated with lysates of HTLV-III-infected H9 cells that were metabolically labeled with [$^{35}$S]methionine or [$^3$H]glucosamine. Induction of antibody was demonstrated by immunoadsorption of gp120 with serum only from mice which were inoculated with the HTLV-III env recombinant.

These results clearly demonstrate that recombinant vaccinia virus synthesizes, processes and transports HTLV-III env proteins to the plasma membrane without expression of other retrovirus genes. In all respects, the env proteins synthesized by recombinant vaccinia virus were indistinguishable from authentic HTLV-III proteins. This is the first demonstration of the preparation of complete native HTLV-III env proteins by recombinant DNA methods. Since the HTLV-III env proteins made are free of other HTLV-III proteins; it is now possible to determine whether the env proteins are targets of cell-mediated immunity and to obtain polyclonal and monoclonal antibodies to the env protein, and to test whether env proteins can be used for immunoprophylaxis against AIDS.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. An infectious recombinant vaccinia virus, comprising an HTLV-III envelope gene under the transcriptional control of a vaccinia virus promoter, wherein said gene is inserted into a non-essential site of a vaccinia virus genome and said promoter is derived from a region other than said non-essential site, such that an infectable host cell infected by said virus expresses HTLV III envelope proteins comprising gp41, gp120 and gp160 and transports one or more of said proteins to the plasma membrane of said host cell.

2. The virus of claim 1 capable of inducing in a susceptible host antibodies having specific affinity to HTLV-III envelope proteins when said virus is administered to said host in an effective amount to immunize said host.

3. The virus of claim 1 wherein said envelope proteins are recognized by sera obtained from patients suffering from HTLV-III infection.

4. The virus of claim 1 having the identifying characteristics of ATCC VR2130.

5. A method of producing HTLV-III envelope proteins comprising growing recombinant vaccinia virus of claim 1 in a medium containing cultured cells which support the multiplication of said virus and recovering from said cultured cells or medium the HTLV-III envelope proteins expressed in the cells by the virus.

* * * * *